(12) United States Patent
Nies

(10) Patent No.: US 8,741,982 B2
(45) Date of Patent: Jun. 3, 2014

(54) BIOACTIVE BONE CEMENT AND METHOD FOR THE PRODUCTION THEREOF

(75) Inventor: Berthold Nies, Fränkisch-Crumbach (DE)

(73) Assignee: InnoTERE GmbH, Radebeul (DE)

( * ) Notice: Subject to any disclaimer, the term of this patent is extended or adjusted under 35 U.S.C. 154(b) by 793 days.

(21) Appl. No.: 11/914,382

(22) PCT Filed: May 9, 2006

(86) PCT No.: PCT/EP2006/004330
§ 371 (c)(1),
(2), (4) Date: Nov. 13, 2007

(87) PCT Pub. No.: WO2006/122678
PCT Pub. Date: Nov. 23, 2006

(65) Prior Publication Data
US 2008/0194729 A1 Aug. 14, 2008

(30) Foreign Application Priority Data
May 13, 2005 (DE) .......................... 10 2005 023 094

(51) Int. Cl.
*A61L 24/06* (2006.01)
*A61K 6/083* (2006.01)
*A61K 6/08* (2006.01)
*A61F 2/28* (2006.01)
*A61K 9/14* (2006.01)
*C08L 33/12* (2006.01)
*C08L 31/02* (2006.01)

(52) U.S. Cl.
USPC ........... 523/116; 523/113; 523/114; 523/115; 623/23.62; 424/487; 424/423; 524/533; 524/560

(58) Field of Classification Search
CPC ......... A61L 27/16; A61L 24/04; A61L 24/06; A61F 2002/4631
USPC .......... 523/115, 116, 118, 113, 114; 433/226, 433/228.1; 623/23.62; 424/487, 423; 524/533, 560
See application file for complete search history.

(56) References Cited

U.S. PATENT DOCUMENTS 4,093,576 A * 6/1978 deWijn ......................... 523/114
4,268,639 A * 5/1981 Seidel et al. .................. 525/303

(Continued)

FOREIGN PATENT DOCUMENTS

| EP | 425200 A1 * | 5/1991 |
| WO | 96/39107 A1 | 12/1996 |
| WO | 98/29145 A1 | 7/1998 |

OTHER PUBLICATIONS

Material Safety Data Sheet: "Calcium Chloride".*

(Continued)

*Primary Examiner* — Michael Pepitone
(74) *Attorney, Agent, or Firm* — Gudrun E. Huckett

(57) ABSTRACT

A bioactive and osteoconductive bone cement is produced from polyacrylates or polymethylacrylates by addition of small amounts of polymerizable monomers containing anionic groups which cause the cement surface to mineralize after being incubated in simulated body fluid. The obtained mineralized layers contain calcium phosphate phases such that the formation of fibrous intermediate layers is prevented once the bone cement has been implanted in bones. Optionally, other additives, e.g. biocompatible calcium salts, biocompatible buffering substances, or x-ray contrast agents, antibiotics, antimicrobial agents, and/or anti-inflammatory agents can be added in order to improve the properties of the cement for individual purposes. The bone cement can be used for anchoring prosthesis components in the bone, stiffening bones, filling and reconstructing all types of bone defects, as dowels for bone screws, or as an implant material for anchoring screws and other implants used for osteosynthesis.

16 Claims, 2 Drawing Sheets

(56) References Cited

U.S. PATENT DOCUMENTS

| | | | |
|---|---|---|---|
| 4,373,217 | A | 2/1983 | Draenert |
| 4,499,251 | A | 2/1985 | Omura et al. |
| 4,537,940 | A | 8/1985 | Omura et al. |
| 4,853,225 | A * | 8/1989 | Wahlig et al. ............... 424/423 |
| 5,142,008 | A * | 8/1992 | Holle et al. ............... 526/193 |
| 5,264,215 | A * | 11/1993 | Nakabayashi et al. ........ 424/423 |
| 5,650,108 | A * | 7/1997 | Nies et al. ............... 264/122 |
| 6,005,162 | A * | 12/1999 | Constantz ............... 128/898 |
| 6,160,033 | A * | 12/2000 | Nies ............... 523/116 |
| 6,300,390 | B1 * | 10/2001 | Angeletakis ............... 523/116 |
| 6,818,682 | B2 * | 11/2004 | Falsafi et al. ............... 523/116 |
| 6,953,594 | B2 * | 10/2005 | Lee et al. ............... 424/602 |
| 7,150,879 | B1 * | 12/2006 | Lee et al. ............... 424/422 |
| 2002/0016384 | A1 * | 2/2002 | Moszner et al. ............... 523/115 |
| 2006/0088476 | A1 * | 4/2006 | Harder et al. ............... 424/9.411 |
| 2006/0096504 | A1 | 5/2006 | Grover et al. |

OTHER PUBLICATIONS

Miyazaki et al.: Bioactive PMMA bone cement prepared by modification with methacryloxypropyltrimethoxysilane and calcium chloride; J. Biomed. Mater. Res. 2003, 67A(4), pp. 1417-1423.

Gilbert et al.: Self-reinforced composite poly(methyl methacrylate): static and fatigue properties; Biomaterials 16 (1995) 1043-1055.

Van Hoyten-Corstjens et al.: Mechanical Behaviour of a new acrylic radiopaque iodine-containing bone cement; Biomaterials 25 (2004) 2657-2667.

Saha et al.: Improvement of mechanical properties of acrylic bone cement by fiber reinforcement; J. Biomechanics vol. 17, No. 7, pp. 467-478 (1984).

Fujita et al.: Bioactive bone cement: Effect of the amount of glass-ceramic powder on bone-bonding strength; J. Biomed. Mater. Res. 40, 145-152 (1998).

Shinzato et al.: Bioactive bone cement: Effects of phosphoric ester monomer on mechanical properties and osteoconductivity; J. Biomed. Mater. Res. 56, 571-577 (2001).

Kjellson et al.: tensile properties of a bone cement containing non-ionic contrast media; J. Material Science Materials in Medicine 12 (2001) 889-894.

Belkoff et al.: Biomechanical evaluation of new bone cement for use in vertebroplasty; Spine vol. 25, No. 9, pp. 1061-1064.

* cited by examiner

BIOACTIVE BONE CEMENT AND METHOD FOR THE PRODUCTION THEREOF

This application is a 35 U.S.C §371 U.S. National Stage Application of International Application No. PCT/EP06/04330, filed May 9, 2006, claiming priority of German Application No. 10 2005 023 094.6, filed May 13, 2005.

BACKGROUND OF THE INVENTION

The aim of the present invention was to provide a novel bone cement, based on poly(methyl methacrylate) (PMMA), copolymers, and analogous systems which cure by radical polymerization, containing additives that cause the cement surface to mineralize upon incubation in simulated body fluid, and in which the mineralization layers obtained contain calcium phosphate phases such that the formation of fibrous intermediate layers is prevented once the bone cement has been implanted in bone.

Polymer-based bone cements are well known and are used, for example, in orthopedics, trauma surgery, and/or spine surgery, as well as in oral and maxillofacial surgery, for the filling and bridging of bone defects and for the fixation of implants. Their advantage over other standard materials such as e.g. metal implants, mineral bone cements based on calcium phosphates, calcium phosphate-based bone substitute materials, and alternative treatment options is that they are easy to handle, rapidly attain final strength (10-30 min.), have high fatigue strength and stability, are relatively well tolerated (sufficient biocompatibility), are freely moldable, and are in general a comparatively cost-efficient application in many fields concerned with bone surgery. Although these high quality materials have been in clinical use for more than 40 years, only few innovative approaches in the field of polymer-based bone cements have been introduced into clinical practice in recent years. As examples for current research approaches, the following directions of work shall be mentioned:

Improvement in handling by substituting powder-liquid mixing systems with 2-paste systems,
  Belkoff et al; Biomechanical Evaluation of a New Bone Cement for Use in Vertebroplasty. Spine. 25(9): 1061-64, May 1, 2000.
reinforcement through fiber addition,
  Saha S.; Pal S. Improvement of mechanical properties of acrylic bone cement by fibre reinforcement. J. Biomech. 17:467-478. 1984;
  Gilbert et al. Self-Reinforced composite poly(methyl methacrylate): Static and fatigue properties. Biomaterials. 16:1043-1055. 1955.
alternative x-ray contrast media
  Van Hooy-Corstjens et al. Mechanical behavior of a new acrylic radiopaque iodine-containing bone cement. Biomaterials, 25, 2657-2667, (2004);
  Kjellsson et al. Tensile properties of a bone cement containing non-ionic contrast media. J Mater Sci Mater Med. 2001 October-December: 12 (10-12): 889-94
addition of various filler and carrier substances,
  Liebendörfer et al. Experimental studies on a new bone cement: Hydroxyapatite composite resin. The 21$^{st}$ Annual Meeting of the Society for Biomaterials. San Francisco. USA, 335. 1995.
  Shinzato et al.: Bioactive bone cement: Effect of phosphoric ester monomer on mechanical properties and osteo-conductivity in J. Biomed. Mater. Res. 2001; 56(4); 571-577.
  Miyazaki et al.: Bioactive PMMA bone cement prepared by modification with methacryloxypropyltrimethoxysilane and calcium chloride. J. Biomed. Mater. Res. 2003; 67A(4); 1417-1423.
  Fujita et al.: Bioactive bone cement: Effect of the amount of glass-ceramic powder on bone bonding strength. J Biomed Mater Res. 1998 April; (1):145-52

Published approaches concerned with the bioactivation of bone cements are based exclusively on the addition of bioactive substances to the polymeric matrix, mostly using very high filling levels (composite cements). In contrast, the aspects of biocompatibility and bioactivity/osteoconductivity of conventional polymer-based bone cements have so far scarcely received attention and even if the products applied to date are, in fact, basically biocompatible and do not generate any pronounced foreign body reactions, they still have the great and distinct disadvantage that they are not sufficiently bioactive to enable direct bonding with bone, that is intergrowth with the same. Osteoconductivity is given, by definition, only when bone is able to actively incorporate the implanted material and directly grows on its surface without creation of a fibrous intermediate layer or is able to cover the same without formation of an intervening gap. These fibrous intermediate layers are formed in the case of all hitherto known polymer-based (conventional) bone cements due to insufficient integration. The fibrous or connective tissue-like intermediate layer can also be seen as a scar tissue with which the body segregates itself from the environment or from a foreign body after an injury. Such layer systems, bone—fibrous intermediate layer—implanted material, have the great disadvantage that they are mechanically unstable, thus causing micromovements which eventually may lead to rejection of the implant, i.e. to so-called implant failure.

Therefore the success of implantations, when polymer-based bone cements are used, strongly depends on a close interlocking of the cancellous bone and the paste-like cement dough during implantation. It is precisely this necessity that sets a considerable limitation to the application field of polymer-based bone cements. This disadvantage is all the more significant, in view of the many alternative and competing implant materials that have meanwhile been equipped with osteoconductive surfaces, e.g. metal implants with bioactive coatings, bone mineral cements based on calcium phosphates, calcium phosphate-based bone substitute materials.

Distinctions from Prior Art:

The patent search on bioactive PMMA cements (PMMA=poly(methyl methacrylate) delivered no search hits or references. Bioactive PMMA cements are described in the literature exclusively as composites comprising a PMMA cement and filling substances made of bioactive glass or hydroxyapatite.

Of particular interest in this context is the publication of Shinzato et al.: Bioactive bone cement: Effect of phosphoric ester monomer on mechanical properties and osteoconductivity in J. Biomed. Mater. Res. 2001; 56(4); 571-577. As distinguished from the present invention (described further below), the phosphoric ester monomer, in this example of Shinzato, is also not added to a classical PMMA cement, but is added as an adhesion promoting agent to a PMMA-Bioglass composite cement. The effect on the mechanical properties and bioactivity has been described as positive. The authors interpret the found results as being the effect of the decreased polymerization tendency of the phosphoric ester monomer (PE) as compared to MMA (MMA=methylacrylate), which ultimately leads to an enrichment or stronger exposition of the bioactive glass particles at the cement surface. This publication contains no reference regarding the bioactive property of the PE monomer and other monomers according to the invention in classical PMMA cements. The bioactive effect is exclusively attributed to the bioactive glass particles.

The work of Miyazaki et al.: Bioactive PMMA bone cement prepared by modification with methacryloxypropyl-trimethoxysilane and calcium chloride (J. Biomed. Mater. Res. 2003; 67A(4); 1417-1423), describes the formation of apatite on appropriately modified cements after incubation in SBF (SBF=simulated body fluid). However, the concentrations said to be necessary are so high that both setting behavior as well as the mechanical properties of the resulting cement are deteriorated considerably.

Neither publication anticipates the experimental results we obtained in the context of the present invention, nor do they suggest the same, particularly, as in the work of Shinzato, bioactivity is ascribed to the addition of bioactive glass at approximately 70 wt %. In the work of Miyazaki, apatite formation on the cement surface is only established after addition of more than 16% $CaCl_2$. In contrast, in our experiments related to the present invention, the desired bioactive effect has been found and verified even after adding only a small amount of a monomer according to the invention such as e.g. methacrylic acid, or ethyleneglycol methacrylate phosphate, at a percentage under 10 weight percent, however, preferably under 5 weight percent and, in particular, under 3 weight percent, without addition of $CaCl_2$. According to our invention aimed at providing an improved bioactive bone cement, the primary effect lies in the formation of crystallization seeds supported by the spontaneous release of calcium ions from the soluble calcium salts added to the bone cement and the short term increase in the local pH value to neutral and slightly basic values. This surprising and also unexpected effect has not been observed in any of the hitherto known bone cements or specifically polymer-based bone cements.

Cortoss®, a product of Orthovita, is currently the sole known polymer-based bone cement on the market that claims to be bioactive. This is a composite material comprised of a curing polymeric matrix with a high filler content of particulate Bioglass. Wherever the bioactive glass particles are present on the surface of the cement, the bioactivity of the Bioglass takes effect. The polymeric matrix itself, even in this case, is not bioactive, in contrast to the present invention. The essentially high proportion of bioactive filler material of up to 70 wt % in said cement—as well as in some known experimental composites from other sources (see above)—is coupled with considerable disadvantages with respect to cement properties that are relevant to and indispensable for a range of notable clinical indications. Of great consequence are changes in the mechanical data and in this case, in particular, the greatly increased stiffness (elastic modulus) together with decreased flexural strength. Due to this brittleness, Cortoss® is unsuitable for the fixation of joint implants. Further disadvantages are that these types of cements have to be designed as 2-paste systems, since the solid und liquid components cannot be mixed in the conventional manner. To be noted, in particular, are the resulting problems such as the sedimentation of the Bioglass filler material and the continuous premature degradation of the radical starter before the curing reaction (during storage). Both problems considerably limit shelflife and necessitate permanent storage in a refrigerator. In said cement, the utilized macromer curing systems are based on the polymer component Bisphenol A (Bis-GMA=bisphenol A glycidyl methacrylate), which is potentially more toxic than the conventional methyl methacrylate. A further great disadvantage of such cements based on novel polymer compositions (in the application as implant material) is the lack of long-term experience compared to the products used from the group of conventional PMMA bone cements which, however, are all not bioactive.

The objective and aim of the present invention therefore, is to find a way to achieve a bioactive/osteoconductive cement surface that develops not only rapidly, but also permanently after or during mixing and implantation, thereby retaining the other relevant properties of the source cement without unfavorably influencing the same, as previously described in the case of Cortoss®. It is familiar to those skilled in the art that the amount of components added to achieve bioactivity should be small. Thus the adopted research approach was contradistinctive to such 2-paste cement systems like Cortoss®, which for the purpose of bioactivity is modified in such a way that with the help of very high filler contents a sufficiently high amount of bioactive particles is presented at the implant surface.

A well-known principle for surface bioactivation of materials in bone contact is the creation of calcium phosphate phases on the material surface through coating or other processes, especially in the case of metals (HA plasma spraying or electrochemically deposited coatings—BoneMaster).

Mineralization of gelatine, R. Kniep, S. Busch, Angew. Chem., 1996, 108, 2788

Mineralization of collagen, S. Rössler et al. Mineralised collagen coating as a biomimetic approach to implant surfaces. Biomaterials 2004.

Kokubo et al. Apatite formation on non-woven fabric of carboxymethylated chitin in SBF. Biomaterials, 2003.

Kawai et al. Coating of an apatite layer on polyamide films containing sulfonic groups by a biomimetic process. Biomaterials, 2003

However, what has always been disadvantageous for the known synthetic polymers concerning feasibility in their use in technical/medical applications—as far as they are at all suitable as implant material—is that they either have to be pretreated chemically so as to obtain acidic groups on the surface that function as crystallization seeds, and/or it is necessary to include calcium salts, as in the example of Miyazaki et al., in which apatite formation on the cement surface could only be achieved after addition of more than 16% $CaCl_2$. With these modifications, to a greater or lesser extent, the synthetic polymers also demonstrated a good mineralization with calcium phosphate phases after incubation in simulated body fluid such as e.g. SBF (simulated body fluid, recipe see below), which would suggest that the respective mineral phases are also created in vivo after implantation.

Cement-like, polymer-based preparations that are potentially capable of surface mineralization in SBF are hitherto unknown in the literature, the reason being, apparently, that the known approaches are not practicable in cements, because in contrast to prefabricated implants, the surface of a cement is developed only in the course of the mixing process or during or after introduction into the body. It is absolutely imperative and a basic principle of the present invention that approaches to bioactivate cement surfaces therefore, must also take effect on the surface in the course of the cement curing process in said manner. The actual mineralization process may preferably then follow in vivo which, however, should commence as rapidly as possible so that adjacent bone cells are offered an attractive environment for adhesion in the early phase soon after implantation.

SUMMARY OF THE INVENTION

In accordance with the present invention, it has now surprisingly been found that the addition of small amounts of polymerizable monomers containing anionic groups influences the surface properties of polymer-based bone cements in such a way that sample specimens made from bone cements modified accordingly, spontaneously are covered by a layer consisting of calcium phosphate phases after incubation in SBF. The required amount of monomers containing anionic groups added to otherwise unchanged polymer-based bone cements is dependent on the choice of the respective monomer, but as a rule lies under 10 weight percent related to the total mass of the cement preparation and preferably under 5 weight percent related to total mass, but still more preferably in the range of 0.03% and 3% related to the cement mass. Monomeric compositions may also be used, but pure monomers are preferred.

The simplest monomer according to the invention is methacrylic acid; further monomers are acrylamide glycolic acid, ethyleneglycol methacrylate phosphate, sulfopropyl methacrylate, 2-acrylamido-2-methylpropane sulfonic acid. These examples are selected monomers from different groups. A detailed description of the principle of the invention and the selection of monomers derived therefrom will follow, so that it will be clear to the expert in the field which additives shall be considered as pertaining to the invention, even though they are not explicitly mentioned here.

The discovered effect confirms that appropriately modified conventional polymer-based bone cements or appropriately equipped novel cement compositions based on polymer-based bone cements exhibit high bioactivity after implantation into the body which causes them to be covered with a calcium phosphate layer and, in this way, renders them osteoconductive. Thus, said improvement, achieved by the present invention, will enable us to prepare polymer-based bone cements that are osteoconductive and can firmly bond to bone tissue—without the adversarial formation of fibrous intermediate layers or other intermediate gaps.

An object of the invention therefore is a bone cement based on poly(methyl methacrylate) (PMMA), copolymers and analogous systems that cure by radical polymerization, but characterized in that they contain additives that cause the cement surface to mineralize after being incubated in simulated body fluid and in which the obtained mineralized layers contain calcium phosphate phases such that the formation of fibrous intermediate layers is prevented after implantation in bones.

The bone cements according to the invention are further characterized in that they have mineral depositions formed thereon in simulated body fluid, of which more than 80% is comprised of precipitated hydroxyapatite, or calcium-deficient hydroxyapatite, and/or substituted carbonated hydroxyapatite, and/or Na, K, or Mg-substituted hydroxyapatite. The bone cements contain an additive (hereinafter additive 1) which can function as mineralization seed for heterogeneous nucleation and the deposition of mineral layers and, in particular, of calcium phosphate phases.

Another object of the invention is a bone cement wherein the additive 1 contains at least one polymerizable monomeric unit such as e.g. acrylate, methacrylate, vinyl, or other ethylenic unsaturated double bonds, or which contains oligomers or copolymers that have been produced using the aforementioned monomers.

Monomers according to the invention (as additives in polymer-based bone cements) on the one hand, contain at least one ethylenic unsaturated double bond by which the monomer molecule can be integrated into the polymeric matrix during radical polymerization, on the other hand, contain at least one anionic group which after completed polymerization can function as a crystallization seed on the cement surface for the mineralization process in vivo. Both functional groups may be combined via molecular parts varying in their chemical composition.

The composition of the polymerizable functionality of the monomer can vary and may contain essentially one or more groups that are susceptible to radical polymerization and that can be modified with an anionic group, directly, or via a spacer molecule. Preferably, radical polymerization will start under environmental conditions, but may be initiated through a heat or light source, etc. Furthermore, the polymerizable functionality of the monomer can contain one or more olefinic unsaturated double bonds without the scope and nature of the invention being changed. Preferred groups of said monomeric unit are acrylate and methacrylate groups, as well as vinyl, and styrol derivatives. Explicitly included are monomers that contain more than one methacrylate or vinyl and/or styrol group.

Alternatively, the additives according to the invention can be bound to the cement matrix via secondary valences instead of covalent binding to the bone cement. The polymerizable functionality can therefore be substituted by molecular parts that are compatible with the cement matrix and for this reason build lasting bonds, with it. Appropriate molecular parts can therefore basically consist of all types of compositions that fulfill this requirement. Particularly suitable are components that are related to the polymeric matrix of the cement. Examples to be mentioned here, are, most notably, the oligomers and polymers of (meth)acrylate, vinyl or styrol, as well as their cooligomers and copolymers formed among themselves and with other radically polymerizable monomers, as known from the polymer industry. According to the invention, the said compounds contain at least one functionality, either directly bound or via a spacer, that can be dissociated or hydrolyzed to form an anionic group.

A spacer is an optional or essential molecular part by which a polymerizable group is/can be bound to an anionic group. The said spacer can thereby have practically any composition that is not in contradiction to the nature of the invention. The spacer can greatly influence, in particular, the compatibility of the added monomer (e.g. solubility and polymerization speed) with other liquid components of the cement. A prerequisite is that the spacer itself and its bonding with other functionalities (the polymerizable part of the molecule and the anionic group) remain chemically stable and physiologically harmless under storage conditions. Possible spacers are notably branched or unbranched hydrocarbon compounds with 1-18 C atoms, short chain polyethers, short chain polyesters (each with 1-12 units, e.g. PEG and PPG), polyaminoacids (e.g. polyamino hexanoic acid), aromatic compounds with one or more benzol rings or similar.

A determinative feature of the invention is most notably the molecular part of the monomeric additive that under physiological conditions is able to dissociate or hydrolyze into an anionic group (anionic functionality), since ultimately, it is the said molecular part that is essential for the formation of crystallization seeds on the cement surface. In experiments relevant to the present invention, this said effect according to the invention has been verified using numerous examples of monomers containing carboxyl, phosphate, phosphonate and sulfate groups (see examples). The anionic functionality, however, can in each case contain also more than one of the aforementioned groups, i.e. combinations of carboxy, phosphate, phosphonate, sulfate and/or other suitable anionic groups without departing from the nature of the invention or changing the observed effect. Besides monomers containing free dissociatable anionic groups, also such compounds are included that are hydrolyzed to dissociatable anionic groups only upon implantation into the body and upon contact with aqueous solutions, preferably and in particular, esters of the carboxy group, phosphate, phosphonate and sulfate groups. Examples of suitable monomers (additives):

- containing carboxyl groups: Simplest monomer according to the invention is methacrylic acid (which does not contain a spacer), acrylamide glycolic acid
- containing phosphate groups: ethyleneglycol methacrylate phosphate, homologues with more than one ethylene glycol unit
- containing phosphonate groups: ethyleneglycol methacrylate phosphonate, homologues containing more than one ethylene glycol unit
- containing sulfate groups: Sulfopropyl methacrylate, 2-acrylamido-2-methylpropane sulfonic acid The mentioned examples for additive 1 shall demonstrate the possible embodiments of the invention on the basis of simple solutions, but are not to be considered as limitations in any way. More complex additives that contain one or more of the aforementioned functionalities and/or contain further functionalities not aforementioned (for example functionalities derived from biological molecules) are explicitly to be considered as additives according to the invention, if they bind to the cement matrix or adhere thereon and, after incubation of cement samples containing said additives in simulated body fluid, cause mineralization of the cement surface.

Still another object of the invention is a bone cement wherein the additive 1 has a functionality through which it is integrated into the cement matrix during the curing or polymerization process or is adsorbed to the same and wherein the additive 1 demonstrates a functionality that can be dissociated or hydrolyzed into an anionic group under physiological conditions and in which these two functionalities are combined directly or via a spacer segment. The additive 1 is preferably contained at an end concentration of 0.01 to 10 weight percent, more preferably at 0.01 to 5 weight percent in the total mass of the hardened bone cement. Still more preferably, the concentration range lies between 0.03 and 3 weight percent of the hardened cement.

One preferred embodiment of the invention is to offer a ready-made bone cement, that as such already contains the additive distributed homogeneously in the monomeric liquid or dissolved in it, or which contains the additive in solid form distributed well and homogeneously into the cement powder.

To enhance the effect according to the invention, further additives may be mixed with the polymer-based cement in order to increase the mineralization tendency of the surface after implantation. This is a possible option, but is not necessary, and therefore is a specific embodiment of the invention.

Water-soluble calcium salts as additive (additive 2) are considered particularly effective, as could be shown in experiments (see examples). The release of $Ca^{2+}$ ions from the near-surface of the cement matrix, locally raises the $Ca^{2+}$ concentration nearby the cement resulting in a more rapid and increased formation of calcium phosphate phases at the seed crystals. Preferred are biocompatible calcium salts, the solubility of which is preferably higher than 1 g/L in water. Examples are: $CaCl_2$, $Ca(NO_3)_2$, calcium acetate, calcium ascorbate, or another calcium salts of natural organic acids found in the organism of animals, or a mixture of such salts. These salts (additive 2) are added in amounts at 0.01 to 20 weight percent, preferably between 0.1 and 10 weight percent. But even more preferred are, in particular, additions of water-soluble calcium salts between 0.1 and 7.5 weight percent.

Other additives according to the invention are buffering substances (additive 3), which by being released at the cement surface, locally cause a pH value increase. Due to the pH-dependent solubility and crystallization of calcium phosphate phases, the increase of the local pH causes a stronger rise in relative supersaturation with regard to calcium phosphate phases formation compared to the solubility product and promotes the precipitation of hydroxyapatite (or Ca-deficient and carbonated hydroxyapatite). Suitable pH-increasing buffering substances (additive 3) are mainly and preferably $Na_2CO_3$, $NaHCO_3$, $Na_3PO_4$, $Na_2HPO_4$, $Na_3Citrat$ (or the respective potassium salts)—but, in principle, all biocompatible buffering substances that have their highest buffering capacity in the neutral or slightly basic range, but preferably those buffering substances with pK values at or higher than 7.4. The buffering substances are added in an amount ranging between 0.1 and 15 weight percent, but preferably between 0.1 and 10 weight percent of the total cement mass. Still more preferable are additions of buffering substances in the range between 0.1 and 7.5 weight percent.

The total amount of additives according to the invention (additives 1 to 3) without x-ray contrast media and antibiotics) is preferably lower than 20 weight percent based on the total mass and still more preferably under 10 weight percent, 0.03 to 3 weight percent being particularly preferred in the case of additive 1, and 0.1 to 7.5 weight percent in the case of additive 2, and 0.1 to 7.5 weight percent in the case of additive 3.

A still further object of the invention is a bone cement, wherein the additives according to the invention and other cement components are formulated as 2-paste or multipaste cement systems and wherein said additives are either suspended or dissolved in the polymer paste.

In addition, the bone cements according to the invention may contain further additives such as e.g. x-ray contrast media, antibiotics, or other antimicrobial agents, and/or anti-inflammatory agents that are capable of inhibiting inflammation reactions in the body after cement implantation.

A further embodiment of the invention are bone cement formulations which are formulated in closed or partially closed mixing systems and/or are available as ready-made, sterilized systems. Another embodiment of the invention also includes bone cement formulations composed as a kit containing two or more components, separately packaged, and aligned in their proportions to one another, and which are combined and mixed just before application.

A final embodiment of the invention is the application of the bone cement according to the invention for anchoring prosthesis components in the bone, for stiffening bones, for filling and reconstruction of bone defects, as dowels for bone screws or as implant material for the anchoring of screws, and other implants used for osteosynthesis.

BRIEF DESCRIPTION OF THE DRAWINGS

The inventive approach and its solution to the state of the art problem are shown in more detail in the following descriptions, figures and examples. The following descriptions, figures and examples are to be understood only as means for exemplifying the invention and are not limiting the invention in any way.

-continued

Figure 2:
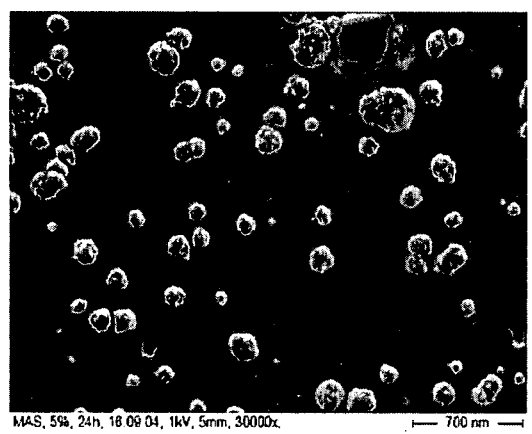
Figure 3A:
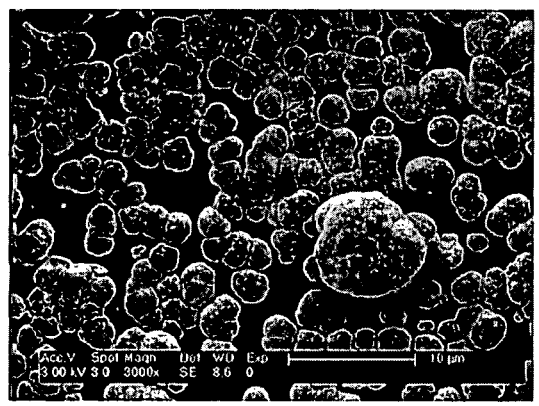
Figure 3B:
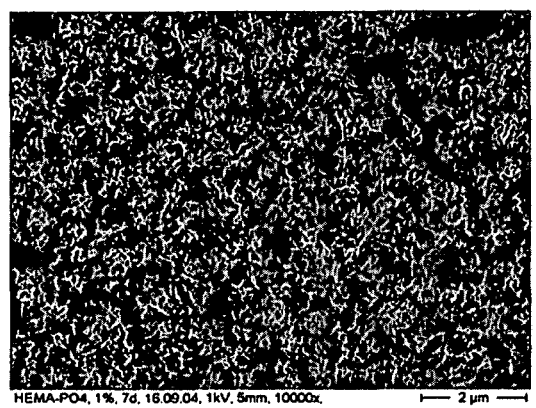
Figure 4:
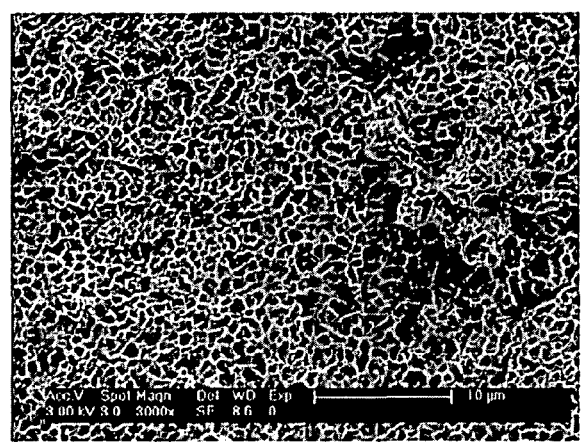

FIG. 2 is a scanning electron microscopy image of a bone cement (Palacos R) with addition of 5% methacrylic acid (MAA) to the monomer without further additions.
FIG. 3a is a scanning electron microscopy image of bone cement (Palacos R) containing 1% ethyleneglycol methacrylate phosphate (HEMA-P) in the monomer, no further additives, at 2/72.
FIG. 3b is a scanning electron microscopy image of bone cement (Palacos R) containing 1% ethyleneglycol methacrylate phosphate (HEMA-P) in the monomer, no further additives, at 3/168.
FIG. 4 is a scanning electron microscopy image of bone cement (Palacos R) containing 1% HEMA-P in the monomer and 2% CaCl2 added to the powder, no further additives; increased mineralization and earlier transition to the crystalline form are shown, score 3/24.

DESCRIPTION OF PREFERRED EMBODIMENTS

Examples

General Description of the Experiment

Sample specimens, sized 2 mm in thickness and 10 mm in diameter were prepared from commercially available bone cement—Palacos R® (Biomet Merck)—by mixing the cement from the powder and the liquid according to the manufacturer's specifications in the ratio of 2:1 (weight to volume). The resulting cement paste was spread on moisted glass plates into polyethylene frames that in hole diameter and thickness corresponded with the sample dimensions. The samples cured under environmental conditions in this frame and were then removed (taken out of the frame). In the following experiments the sample area that had faced the moist glass plate during the curing process was evaluated. Unmodified bone cement, Palacos R® provided by Biomet Merck, was used as control. The experimental cement compositions differed from the control in that they contained monomers according to the invention added to the cement liquid (examples 1 and 2), and in that soluble calcium salts and buffering substances were added to the powder simultaneously with anionic monomer to the cement liquid (examples 3 and 4).

After preparation, the samples were incubated in 1.5 times concentrated SBF at 37° C. The SBF used was composed as follows: 150 mmol/l NaCl; 4.2 mmol/l NaHCO$_3$; 1.5 mmol/l MgCl$_2$; 1 mmol/l K$_2$HPO$_4$; 5 mmol/l KCl; 2.4 mmol/l CaCl$_2$; pH=7.4. Evaluation was carried out by means of a score utilized to determine sample surface mineralization using scanning electron microscopy images. The sample surfaces were characterized also physically and the chemical composition of the mineral layer and phase composition was determined by x-ray diffraction.

Mineralization Score:

The data represent the extent of mineralization in scores of 0 to 3, with 0 being no mineralization, 1 being isolated, 2 advanced, and 3 being complete mineralization, within the respective incubation time in hours. Thus, 2/24 e.g. stands for advanced mineralization after an incubation period of 24 hours.

TABLE 1

| Time-dependent mineralization | | | | |
|---|---|---|---|---|
| | Time | | | |
| Mineralization | 1 h | 24 h | 72 h | 168 h |
| none (0) | 0/1 | 0/24 | 0/72 | 0/168 |
| isolated (1) | 1/1 | 1/24 | 1/72 | 1/168 |
| advanced (2) | 2/1 | 2/24 | 2/72 | 2/168 |
| complete and crystalline (3) | 3/1 | 3/24 | 3/72 | 3/168 |

Example 1

Figure 1:
FIG. 1    is a scanning electron microscopy image of a bone cement (Palacos R) with addition of 0% methacrylic acid (MAA) to the monomer without further additions (comparative example).

Bone cement (Palacos R) with addition of x % methacrylic acid (MM) to the monomer without further additions.
Result:
0% MM: 0/1, 0/24 (FIG. 1), 0/72, 0/168 comparative experiment (see FIG. 1)
0.5% MAA: 1/24,
1% MAA: 1/24,
2.5% MAA: 1/24,
5.0% MAA: 1/24, (see FIG. 2)
By addition of MAA a relatively low mineralization is achieved, also not showing high concentration dependency.

Example 2

Bone cements (Palacos R) containing x % ethyleneglycol methacrylate phosphate (HEMA-P) in the monomer, no further additives.
Result:
0.5% HEMA-P: 1/24,
1% HEMA-P: 1/1, 1/24, 2/72 (see FIG. 3a), 3/168 (see FIG. 3b)
2.5% HEMA-P: 2/24,
5% HEMA-P: 2/24 (thick layer)
By addition of HEMA-P, a marked mineralization is achieved, even at low concentrations that increases further with rising concentrations. With the length of incubation time the crystallanity of the mineral layer also increases.

Example 3

Bone cement (Palacos R) containing a) 1% HEMA-P and b) 2.5% MM in the monomer and in each 2% CaCl2 added to the powder, no further additives.
a) Increased mineralization and earlier transition to the crystalline form, score 3/24 (FIG. 4; comparable with 5% HEMA-P in example 2).
b) 1/24, tendency towards similarly increased mineralization, difference is less distinct than in the case of HEMA-P.

Example 4

Bone cement (Palacos R®) containing 1% HEMA-P in the monomer and 5% Na$_2$CO$_3$ in the powder, no further additives.
Result: tendency to increased mineralization and earlier attainment of the crystalline state.
(The qualitative evaluation does not allow a more subtle distinction regarding the extent of mineralization)

What is claimed is:

1. A bone cement that cures by radical polymerization, the bone cement consisting of:
- a radically polymerizing bone cement base material of
  - a powder component of polymethylmethacrylate or polymethylmethacrylate copolymers with an initiator for effecting radical polymerization, an opacifier, and optionally a colorant; and
  - a liquid component of methymethacrylate monomers with an activator or a co-initiator for effecting radical polymerization, a stabilizer, and optionally a colorant;
- an additive 1 consisting of monomers, wherein the monomers have free dissociatable or hydrolyzable anionic groups and at least one polymerizable unit, and optionally co-oligomers or copolymers of said monomers;
- optionally an additive 2 of water soluble calcium salts, wherein the solubility of the calcium salts in water is greater than 1 g/l;
- an additive 3 of biocompatible buffering substances having a highest buffering capacity in the neutral to slightly basic range; and
- optionally further additives selected from an x-ray contrast medium, antibiotics, antimicrobial agents, and anti-inflammatory agents;
- wherein said additives 1, 2, and 3 cause mineralization of the cement surface in the form of mineralized layers and the mineralized layers contain calcium phosphate phases.

2. The bone cement according to claim 1, wherein said free dissociatable or hydrolyzable anionic groups in said additive 1 are selected from the group consisting of carboxy, phosphate, phosphonate, and sulfate groups, and biocompatible esters of carboxy, phosphate, phosphonate, and sulfate groups.

3. The bone cement according to claim 1, wherein the monomers of said additive 1 are selected from the group consisting of methacrylic acid, acrylamide glycolic acid, ethyleneglycol methacrylate phosphate and homologues thereof with more than one ethylene glycol unit, ethylene glycol methacrylate phosphonate and the homologues thereof with more than one ethylene glycol unit, sulfopropyl methacrylate, and 2-acrylamido-2-methylpropane sulfonic acid.

4. The bone cement according to claim 1, wherein the calcium salt in said additive 2 is $CaCl_2$, $Ca(NO_3)_2$, $Ca(acetate)_2$, $Ca(ascorbate)_2$, or another calcium salt of a naturally occurring organic acid in an organism of the animal, or a mixture of said salts.

5. The bone cement according to claim 1, wherein said biocompatible buffering substance in said additive 3 is $Na_2CO_3$, $NaHCO_3$, $Na_3PO_4$, $Na_2HPO_4$, $Na_3$-citrate, $K_2CO_3$, $KHCO_3$, $K_3PO_4$, $K_2HPO_4$, or $K_3$-citrate, or consists of a mixture of substances containing one of the said biocompatible buffering substances.

6. The bone cement according to claim 1, wherein said additive 1 is homogeneously mixed with the liquid component of the bone cement or is dissolved in the liquid component of the bone cement, or said additive 1 is finely and homogeneously distributed in the powder component of the bone cement.

7. The bone cement according to claim 1, wherein said additive 1 is contained in a final concentration of 0.01 weight percent to 10 weight percent of the total mass of the hardened bone cement.

8. The bone cement according to claim 1, wherein said additive 2 is contained in a concentration of 0.1 weight percent to 20 weight percent based on a water-free substance of the bone cement and wherein said additive 2 is finely and homogeneously distributed in the powder component.

9. The bone cement according to claim 1, wherein said additive 3 is contained in a final concentration of 0.1 weight percent to 15 weight percent based on a water-free substance of the bone cement.

10. The bone cement according to claim 1, wherein the sum in weight percent of said additives 1 to 3 does not exceed 20 weight percent in the final concentration based on the total mass, wherein the content of said additive 1 is 0.03 weight percent to 10 weight percent, the content of said additive 2 is 0.1 weight percent to 7.5 weight percent, and the content of said additive 3 is 0.1 weight percent to 7.5 weight percent.

11. The bone cement according to claim 1, wherein said additives 1, 2, and 3 are formulated in 2-paste or multiple paste systems and are suspended or dissolved in a polymer paste.

12. The bone cement according to claim 1, wherein the bone cement is formulated in a closed or partially closed mixing system.

13. The bone cement according to claim 1, wherein the bone cement is a ready-made, sterilized system.

14. The bone cement according to claim 1, wherein the bone cement consists of a kit that consists of two or multiple separately packaged components that are matched in their proportions to one another and are combined with each other directly before application.

15. The bone cement according to claim 1, wherein said monomers contain a spacer between said free dissociatable or hydrolyzable anionic groups and said at least one polymerizable unit.

16. A bone cement that cures by radical polymerization, the bone cement consisting of:
- a liquid component consisting of:
  - methylmethacrylate monomers;
  - an activator or a co-initiator,
  - a stabilizer;
  - an additive 1 consisting of monomers, wherein the monomers have free dissociatable or hydrolyzable anionic groups and at least one polymerizable unit, and optionally co-oligomers or copolymers of said monomers;
  - optionally a colorant;
- a powder component consisting of:
  - polymethylmethacrylate or polymethylmethacrylate copolymers;
  - a polymerization initiator;
  - an opacifier;
  - an additive 3 of biocompatible buffering substances having a highest buffering capacity in the neutral to slightly basic range; and
  - optionally an additive 2 of water soluble calcium salts, wherein the solubility of the calcium salts in water is greater than 1g/l;
  - optionally further additives selected from the group consisting of x-ray contrast media, antibiotics, antimicrobial agents, anti-inflammatory agents, and colorants;
- wherein said additives 1, 2, and 3 cause mineralization of the cement surface in the form of mineralized layers and the mineralized layers contain calcium phosphate phases.

* * * * *